United States Patent
Farrow et al.

(10) Patent No.: US 9,689,829 B2
(45) Date of Patent: Jun. 27, 2017

(54) NANOPROBE AND METHODS OF USE

(71) Applicant: New Jersey Institute of Technology, Newark, NJ (US)

(72) Inventors: Reginald C. Farrow, Somerset, NJ (US); Camelia Prodan, Montclair, NJ (US); Alokik Kanwal, Princeton, NJ (US); Gordon A. Thomas, Princeton, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 14/206,191

(22) Filed: Mar. 12, 2014

(65) Prior Publication Data

US 2015/0276649 A1    Oct. 1, 2015

Related U.S. Application Data

(60) Provisional application No. 61/777,969, filed on Mar. 12, 2013.

(51) Int. Cl.
*G01N 27/30*    (2006.01)
*G01N 27/02*    (2006.01)
(Continued)

(52) U.S. Cl.
CPC .......... *G01N 27/308* (2013.01); *C25D 13/02* (2013.01); *G01N 27/02* (2013.01); *G01N 33/483* (2013.01); *G01N 33/48728* (2013.01)

(58) Field of Classification Search
CPC . G01N 27/02; G01N 33/483; G01N 33/48728
See application file for complete search history.

(56) References Cited

U.S. PATENT DOCUMENTS 7,736,979 B2    6/2010    Farrow et al.
7,964,143 B2    6/2011    Farrow et al.
(Continued)

FOREIGN PATENT DOCUMENTS

NL    EP 2256492 A1 * 12/2010 ........... G01N 33/487

OTHER PUBLICATIONS

Yun et al. (Nanotechnology 18, Oct. 2007, 465505).*
(Continued)

*Primary Examiner* — Luan Van
*Assistant Examiner* — Steven E Rosenwald
(74) *Attorney, Agent, or Firm* — Timothy X. Gibson, Esq.; Gibson & Dernier LLP

(57) ABSTRACT

A device for determining the presence of a single cell and/or determining a state of a single cell includes a first nanotube disposed on a first electrode, and a second nanotube disposed on a second electrode, wherein the first and second nanotubes are spaced apart at a length that is smaller than a cell size to be detected. A method for determining the presence of a single biological cell includes sensing impedance between a first nanotube and a second nanotube. A method of manufacturing includes providing a nanotube, providing an electrode coated with an insulating material, wherein an aperture is defined in the insulating material through to the electrode, and using electrophoresis deposition to deposit a nanotube within the aperture and in electrical communication with the electrode.

7 Claims, 7 Drawing Sheets

(51) Int. Cl.
*G01N 33/483* (2006.01)
*C25D 13/02* (2006.01)
*G01N 33/487* (2006.01)

(56) References Cited

U.S. PATENT DOCUMENTS

| | | |
|---|---|---|
| 8,257,566 B2 | 9/2012 | Farrow et al. |
| 8,546,027 B2 | 10/2013 | Farrow et al. |
| 2007/0205707 A1 | 9/2007 | Den et al. |
| 2008/0187915 A1 | 8/2008 | Polonsky et al. |
| 2010/0072459 A1 | 3/2010 | Bertin et al. |
| 2010/0237851 A1* | 9/2010 | Coster .................... G01R 27/28 324/76.19 |
| 2011/0168562 A1 | 7/2011 | Nuckolls et al. |
| 2011/0236984 A1 | 9/2011 | Sun et al. |

OTHER PUBLICATIONS

PCT International Search Report dated Jul. 17, 2014 issued on corresponding PCT International Patent Application No. PCT/US2014/024092.
PCT International Preliminary Report on Patentability dated Sep. 24, 2015.
Written Opinion of the international Searching Authority dated Jul. 17, 2014 issued on corresponding PCT International Application No. PCT/US2014/024092.

* cited by examiner

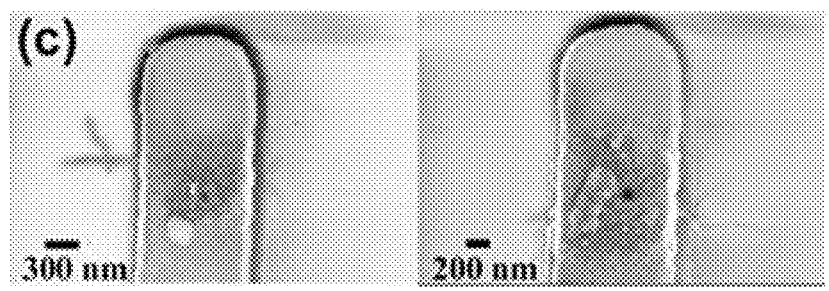
Fig. 1(c)
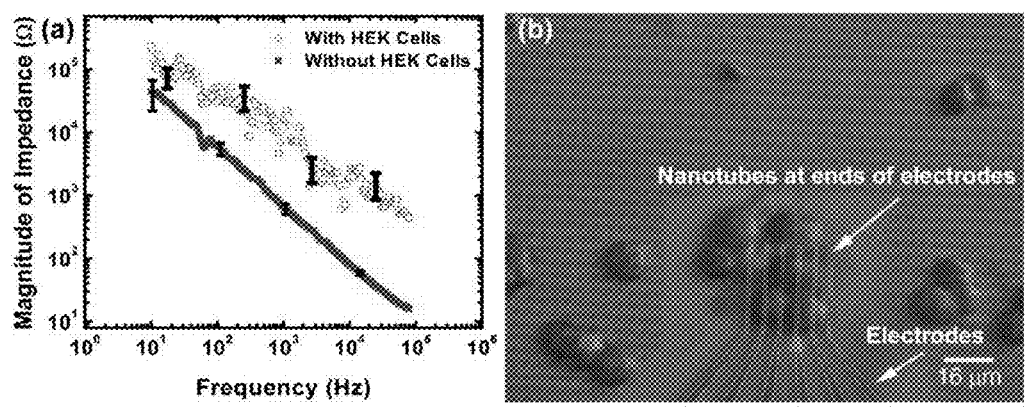
Figs. 2(a)-(b)

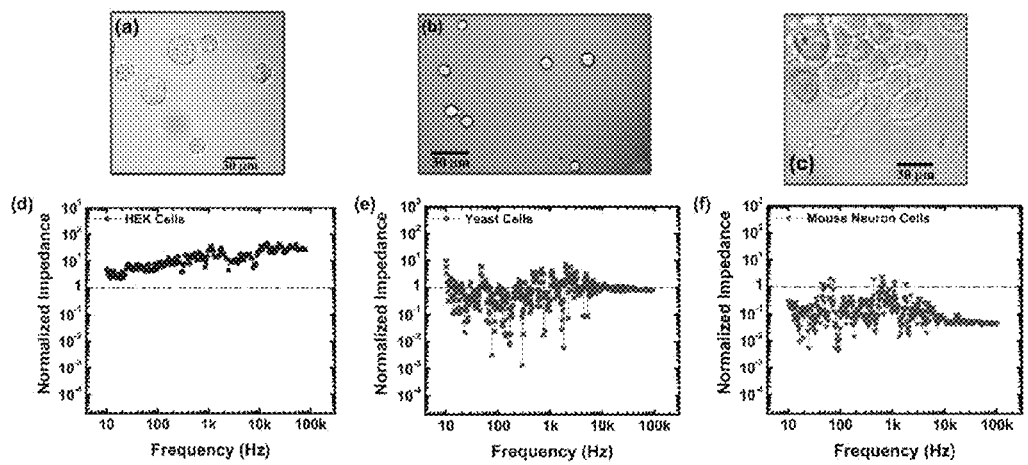
Figs. 3(a)-(f)
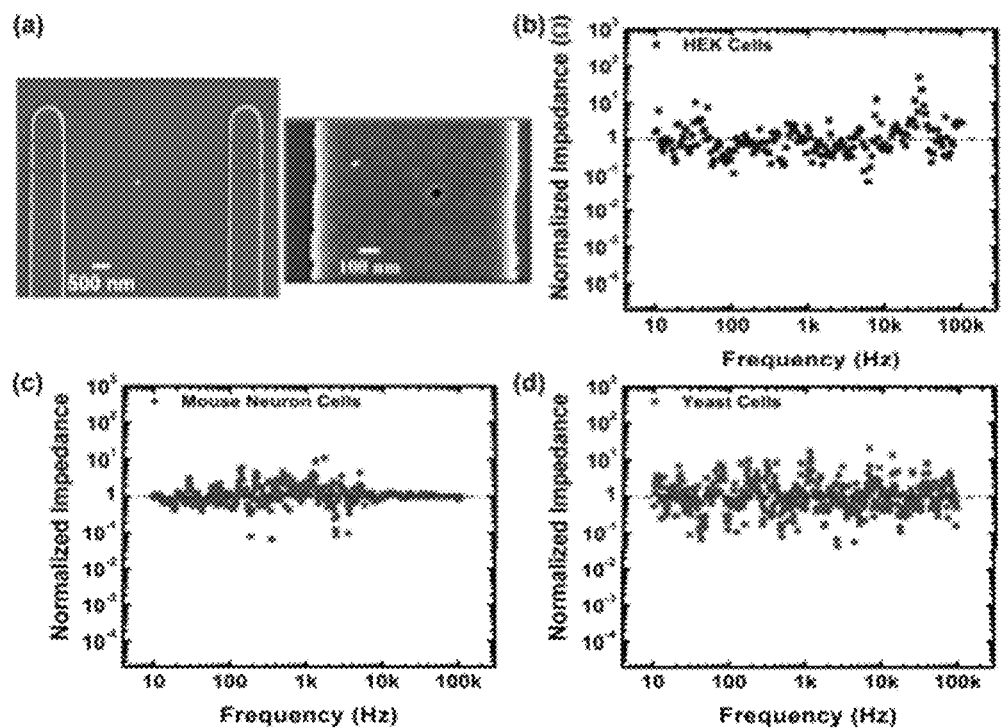
Figs. 4(a)-(d)

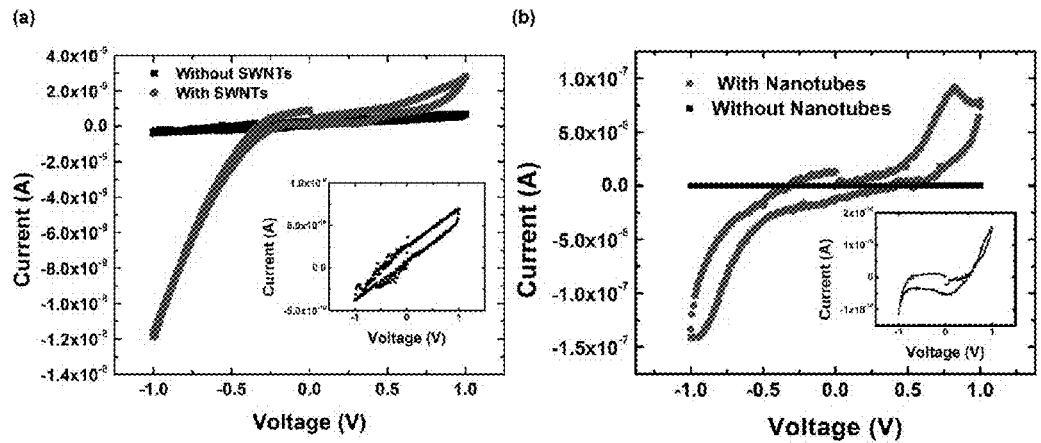
Fig. 7(a)-(b)
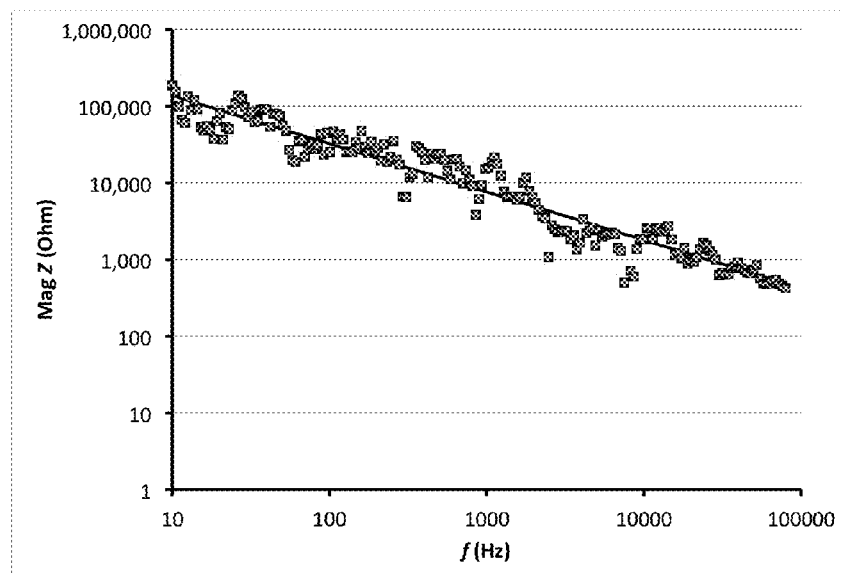
Fig. 8

NANOPROBE AND METHODS OF USE

CROSS-REFERENCE TO RELATED APPLICATIONS

This application claims the benefit of and priority to U.S. Provisional Patent Application No. 61/777,969, filed Mar. 12, 2013, the entire contents of which are incorporated by reference herein.

STATEMENT REGARDING FEDERALLY SPONSORED RESEARCH

The research leading to this disclosure was supported, in part by federal grants including the DARPA Grant(s) FA9550-05-1-0461, FA8650-08-1-7825 and N00014-08-1-0278) Accordingly, the United States Government may have certain rights in the disclosure.

FIELD OF THE DISCLOSURE

This disclosure relates to cell detection, cell identification, bioprobes and carbon nanotubes.

BACKGROUND

Cellular detection and identification are proving vital for the prevention and diagnosis of many diseases related to cancer and both viral and bacterial infections. Techniques for cellular detection can be divided into two main categories, optical and electrical. Optical techniques rely on fluorescence of dyes attached to targeted cells. The dyes emit light when stimulated, allowing for detection through an optical microscope. This technique has proven versatile in detecting small quantities of the targeted cells. However, the use of optical components can be expensive. In addition, the need of mixing the appropriate dyes limits the number of various types of cells that can be identified simultaneously. Also the dyes themselves can be toxic to the cells through a process called phototoxicity.

Many electrical based techniques operate by measuring the change in impedance due to the presence of the target cells. These systems incorporate electrodes that measure the impedance or current between them. Currently there are two mechanisms used for electrical detection and identification of cells. The first method relies on functionalizing electrodes with a bioreceptor, which is designed to be highly selective. These electrodes are immersed into a solution containing the cells. The bioreceptors will bind to the targeted cell, immobilizing them on top of the electrodes. The immobilized cell will change the measured impedance or current either by insulating them or by changing the conductance of the fluid around the electrodes due to an increase in ions that surround the cells.

Microfluidic devices use a much smaller volume of cell suspension than the immersion technique. Electrodes or the walls of the fluidic channel can be functionalized to immobilize the targeted cells. The cell suspension is pumped through the channel and over the electrodes. The functionalized surface would capture cells as they flow over it, reducing the overall volume of suspension that is flowing between the electrodes. This will result in a change in the measured impedance or current between the electrodes.

Another electrical based technique relies on functionalizing magnetic beads with the bioreceptors instead of the electrodes or walls. The beads are mixed with the sample, allowing the targeted cells to attach to them. After which the targeted cells are separated from the suspension by using a magnetic field. The cell-coated beads are then re-suspended in a low conductive media and either placed or flown over electrodes. The entire device is placed in a magnetic field, such that the beads are attracted to the electrode surface. The resulting accumulation of cell-coated beads lowers the impedance to indicate the presence of the targeted cells. Without the cells the drop in impedance is much smaller. This method has an advantage of having a higher sensitivity over the functionalized electrodes or walls since the magnetic beads can better cover the electrodes. However, both techniques still lack the ability to simultaneously detect a larger variety of cells in a single sample, which is required for a rapid general diagnosis.

SUMMARY OF THE DISCLOSURE

In at least one aspect of this disclosure, a device for determining the presence of a single cell and/or determining a state of a single cell includes a first nanotube disposed on a first electrode, and a second nanotube disposed on a second electrode, wherein the first and second nanotubes are spaced apart at a length that is smaller than a cell size to be detected.

The first and second nanotubes can be spaced apart at about 6 microns. In some embodiments, the first and second nanotubes can be spaced apart at less than about 6 microns.

The first electrode and second electrode can expand out into larger dimensions to facilitate external electrical connections or be routed directly to circuitry nearby fabricated on the same substrate to facilitate signal conditioning and/or further routing. Each electrode can be coated with an insulating layer having at least one aperture for each nanotube to be housed therein.

In some embodiments, at least one of the nanotubes rises higher off at least one of the electrodes than the insulating layer is thick, although nanotubes whose length is less than the height of the insulator may also work for this application. The aperture dimensions and aspect ratio can be such as to enable deposition of single nanotubes using electrophoresis. The aperture can be substantially cylindrical and can be about 50 nanometers in diameter. The insulating layer and the aperture can be about 75 nanometers in thickness. The length of the nanotubes in the suspension for electrophoresis deposition can be short enough to facilitate deposition of a single nanotube per aperture. The length of the nanotubes in the suspension used for electrophoresis deposition can be less than 200 nm.

In at least one aspect of this disclosure, a method can include disposing a device in a desired position, the device including a first nanotube disposed therein and a second nanotube disposed therein, and testing a conductance and/or an impedance of the device between at least the first and second nanotubes, or between the first or second nanotube and a reference electrode.

In some embodiments, the desired position can be within an electrolytic fluid, and the method can further include determining whether the nanotubes are disposed properly on the device based on the conductance and/or impedance.

In some embodiments, the desired position is proximate to a biological cell, and the testing of conductance and/or impedance is done between the first nanotube and the second nanotube. The method can further include determining a state of a biological cell based on the conductance and/or impedance.

The method can further include exciting an ion channel of a biological cell with an oscillating electric field, measuring the frequency of a natural rate for that ion, and detecting a local change in conductance in the fluid.

The method can further include fitting an average magnitude of the impedance as a function of frequency to a mathematical function and subtracting the best fit to that function from the impedance to determine fluctuations relative to the average behavior.

The method can further include comparing peaks and troughs of the fluctuations to characteristic rates of ion channels known or suspected to be present. In some embodiments, the determined state can include a cell health or a cell type. The method can further include detecting a membrane potential of the biological cell.

In some embodiments, the desired position is proximate to a biological cell, wherein the testing of conductance and/or impedance is done between the first nanotube and the second nanotube, the method further comprising sensing an impedance between a first nanotube disposed on a first electrode and a second nanotube disposed on a second electrode, wherein the first and second nanotubes are space apart at a distance equal to or less than the size of the biological cell to determine the presence of a single biological cell.

In at least one aspect of this disclosure, a method of manufacturing includes providing a nanotube, providing an electrode coated with an insulating material, wherein an aperture is defined in the insulating material through to the electrode, and using electrophoresis deposition to deposit a nanotube within the aperture and in electrical communication with the electrode. The method can further include selecting the nanotubes to be less than about 200 nanometers in length.

These and other features of this disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices, systems, and methods of the subject disclosure without undue experimentation, embodiments thereof will be described in detail herein below with reference to certain figures, wherein:

FIG. 1(c) shows two zoomed SEM images of nanotubes deposited into a nanoscale hole at the tip of the electrodes;

FIG. 2(a) shows the magnitude of the impedance vs. frequency for two embodiments, wherein the open circles represent HEK cells on top of the electrodes, the squares represent the case without cells, and error bars are plotted for each decade.

FIG. 2(b) is an enhanced optical image during a measurement of HEK cells, highlighting the interconnect metal and nanoprobes in that are underneath the cells; wherein the location of the interconnects (drawn in blue) were ascertained from the CAD file used during device fabrication and added to the original image for clarity.

FIG. 3(a) is a high resolution images of HEK cells;

FIG. 3(b) is a high resolution images of yeast cells;

FIG. 3(c) is a high resolution images of mouse neuron cells

FIG. 3(d) shows the normalized impedance of HEK cells;

FIG. 3(e) shows the normalized impedance of yeast cells;

FIG. 3(f) shows the normalized impedance of mouse neuron cells;

FIG. 4(a) is an SEM image of electrodes without nanotubes, wherein the inset is a zoomed image of the approximately 50 nm apertures used for measurements (highlighted in red).

FIG. 4(b) shows impedance magnitude spectrum for devices without nanotubes for HEK cell;

FIG. 4(c) shows impedance magnitude spectrum for devices without nanotubes for mouse neuron cells;

FIG. 4(d) shows impedance magnitude spectrum for devices without nanotubes for yeast cells.

FIG. 7(a) shows IV (current-voltage) curves of devices recorded using phosphate buffer solution as the conducting medium to a platinum electrode;

FIG. 7(b) shows IV curves for the case were device to device measurements were made;

FIG. 8 shows a plot of experimental data as described herein; and

DETAILED DESCRIPTION OF EMBODIMENTS

The following is a detailed description of the embodiments of this disclosure. Those of ordinary skill in the art may make modifications and variations in the embodiments described herein without departing from the spirit or scope of this disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure.

Aspects of this disclosure create a device that combines the benefits of optical and electrical probes using single-walled carbon nanotubes (SWNTs). In at least some embodiments, no fluorescent dyes are needed and unlike previous electrical techniques the cell does not need to be immobilized with a bioreceptor. Unlike both optical and previous electrical cell detection methods the technique disclosed herein may provide information about the cell type and condition without modification of the cell or the probe because the nanotubes disclosed herein may not functionalized. Embodiments of this disclosure can achieve high spatial resolution without significant disturbance to cells due to the nanoscale size of the SWNTs.

In embodiments of this disclosure, when the SWNT probes are made close enough, sub-cellular resolution of electrical properties down to nanometer scale is achieved to a higher degree than both optical and previous electrical methods. Devices utilizing carbon nanotubes have been successfully fabricated to electrically detect cells or bio molecules; however they have not yet approached the nanoscale while maintaining compatibility with semiconductor fabrication technology. Embodiments of this disclosure include an array of less than about 10 nm diameter nanoprobes that have been fabricated using a process that is fully compatible with current semiconductor technologies. A nanoprobe of the geometry as disclosed herein would generally require either lithography that is beyond the current state of manufacturing technology or thermal cycles that are outside the requirements needed to preserve CMOS logic that will be needed to control the device.

The spacing of devices of certain embodiments of this disclosure can be done in an array on the nano-scale with the current semiconductor technologies. This allows for direct integration with the CMOS logic required for a practical lab-on-a-chip device. To demonstrate the capabilities of embodiments of this disclosure, impedance spectroscopy was used to detect human embryonic kidney cells (HEK), yeast cells, and neuron cells harvested from mice. One ordinarily skilled in the art would appreciate that this disclosure is not limited to these cell types and can be used for any cell detection.

Figure 1A:
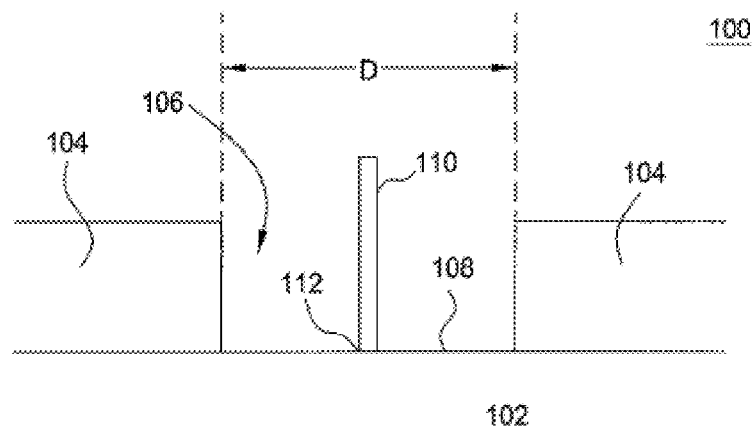
FIG. 1(a) shows is schematic cross-sectional view of a nanotube based structure.
Figure 1B:
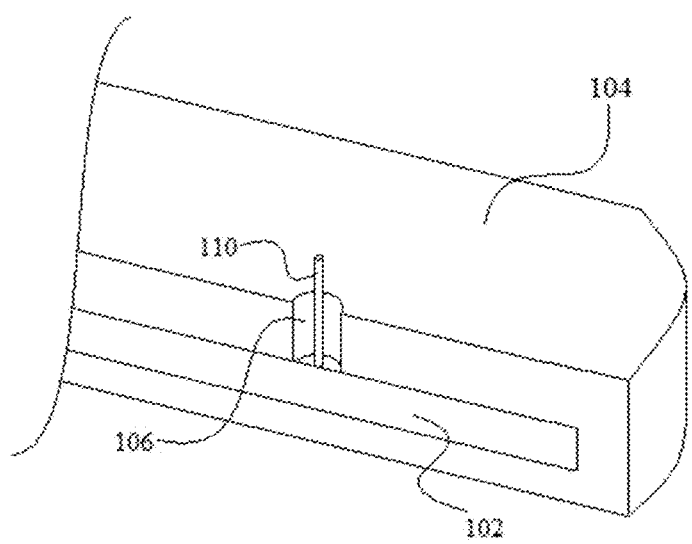
FIG. 1(b) shows a zoomed in schematic of a device including an SWNT 110, shown connected to a metal lead (e.g., electrode 102) through an approximately 50 nm diameter aperture (e.g., aperture 106) in about 75 nm thick nitride layer (e.g., layer 104)

FIG. 1(a) shows a zoomed in schematic cross-sectional view of a portion of a device 100 that can be fabricated using embodiments of this disclosure. FIG. 1(b) shows a perspective cross-section of a portion of a device 100. Suitable manufacturing techniques may also be found at least one of U.S. Pat. No. 7,964,143 to Farrow et al., U.S. Pat. No. 8,257,566 to Farrow et al., U.S. Pat. No. 7,736,979 to Farrow et al., and/or U.S. Pat. No. 8,546,027 to Farrow et al. The device 100 includes one or more electrodes 102, over which an insulating layer 104 is deposited. The insulating layer 104 can be patterned to form an aperture 106, which exposes a top surface of the electrode 102. A one or more of SWNTs 110 can be deposited inside the aperture 106 so that one end 112 of the SWNT 110 contacts the top surface of the electrode 102. The electrode 102 is any suitable conducting material such as a metal and/or a conducting film (deposited over an insulating material) that allows a bias voltage to be applied for electrophoretic deposition of the nanotube 110. Multiple electrodes 102 can be fabricated and coated as branches or arms. The electrodes 102 and/or the SWNTs 110 can be separated by any suitable distance (e.g., from about 100 nm to about 6 microns apart). Also, the electrodes 102 can be included on a single substrate and coated on the single substrate such that device 100 is wafer shape or the like.

In one embodiment of this disclosure, a device was fabricated in a cleanroom by first depositing about a 300 nm thick dielectric layer on top of clean silicon wafers. Next, a layer of photoresist was deposited and patterned using an autostepper. A metal stack comprising of about 20 nm of chrome, about 150 nm of cobalt, and about 50 nm of chrome was subsequently evaporated without breaking vacuum for said embodiment. Lift off was performed to form the metal layer, comprising of six individual about 1 micron wide electrodes with about a 6 micron pitch. Next, for said embodiment about 75 nm of conformal low stress silicon nitride was deposited using plasma enhanced chemical vapor deposition (PECVD). Using reactive ion etch (RIE), apertures 106 for the contact pads were opened in the nitride layer. About 30 to about 50 nm holes were then patterned using e-beam lithography. The apertures 106 were etched using RIE, through the silicon nitride and down to the metal. In said embodiment the wafers were diced, producing about 50 chips per wafer. Chips were subsequently glued to a chip carrier. Handling of the devices and electrical contact were thereby facilitated by wire bonding to the chip carrier's contact pads.

In one embodiment of this disclosure carbon nanotubes were deposited using electrophoresis (FIG. 1(c)), based on a method described above. Purified SWNTs 110 [about 95% metallic] were utilized. In said embodiment, prior to deposition, the nanotubes were horn sonicated for about 6 hours to reduce their lengths. During deposition, about 10 V was applied between the device and a platinum rod [reference electrode], with a spacing of about 1 cm between the rod and the chip. In said embodiment the nanotubes follow the field lines and deposit into the nanoscale holes in the nitride, and connect to the metal, forming the probes. After deposition, the devices are thoroughly rinsed to remove any stray nanotubes.

In testing of certain embodiments of this disclosure three cell types were grown, HEK cells were grown as an adherent culture in a flask. The cells were incubated at about 37° C. in the presence of about 5% $CO_2$ until they were confluent and then harvested. The growth medium used for these cells was Dulbecco's modified eagle medium (DMEM) containing about 10% fetal bovine serum, penicillin streptomycin and about 2 mM L-glutamine. The flasks to test certain embodiments of this disclosure were treated with trypsin and incubated for about 10 minutes. Cells were gently diluted with DMEM to annihilate the effects of trypsin and subsequently used for measurements.

The conductivity of DMEM and HEK cell suspension was approximately $1.5 \times 10^2$ S/cm. Yeast cells were incubated in 3 ml yeast extract peptone glucose (YPD) broth in a shaker at about 30° C. and about 200 rpm for about 48 hours. The cells were then centrifuged at about 1500 times gravity for about 3 minutes. The supernatant was discarded and cells were re-suspended in about 5 mM of 4-(2-hydroxyethyl)-1-piperazineethanesulfonic acid (HEPES) containing about 5 mM glucose and subsequently used for measurements. Conductivity of the suspension containing HEPES buffer and yeast cells was approximately $1 \times 10^{-4}$ S/cm.

Mouse neuron cells were cultured from slices of mouse brain tissue. The tissue is rinsed twice with about 5 mL Hank's buffered salt solution (HBSS). Next, about 5 mL of Trypsin and about 0.15% of deoxyribonuclease (DNAase) is applied to the tissue and then incubated for about 15-25 minutes at about 37° C. and about 5% CO2. The tissue is then rinsed twice with about 5 mL HBSS/fetal bovine serum (FBS) (about 4.5 mL HBSS, about 0.5 mL FBS) solution, followed by rinsing twice with about 5 mL HBSS only. The remaining tissue is triturated with a 1 mL pipette using DMEM. The resulting cell solution is centrifuged for about 3 minutes at about 3000 rpm. The supernatant is removed, and the cells are gently re-suspended in growth media. Next, it is filtered in a three stage process (highly porous, middle porosity, least porous). The final cell suspension is transferred to a new flask for experiments. The resulting cell media contains DMEM, similar to the HEK cells.

In an experiment utilizing embodiments of this disclosure, about 100 µl of a suspension of cells is placed directly on top of the electrodes of certain embodiments of this disclosure. Said electrodes were monitored using an optical microscope. When a cell moved into position over the electrodes, a measurement was taken using a SR785 Stanford Research Systems signal analyzer and a custom built circuit to amplify the signal. Prior to each measurement, the cells were imaged to correlate their position to the electrodes. After a set of experiments was complete, the device was thoroughly rinsed with boiling deionized water to remove any cell residue and prepare it for the next set of experiments. The resulting data was smoothed using a 10-point Savitzky-Golay method with a second order polynomial.

FIG. 2(a) shows the magnitude of the impedance versus frequency for two cases in certain embodiments of this disclosure, one with HEK cells and one without. The data was averaged over nine measurements. The open circles represent the presence of HEK cells over the electrodes and the squares represent the media without cells on the device of one embodiment of this disclosure. Error bars are plotted for each decade to help the legibility of the data.

FIG. 2(b) shows an optical image of an embodiment of this disclosure during a typical measurement with cells on top of the electrodes. In said embodiment, the nanotubes are located on the ends of the electrodes, which are artificially highlighted. Noise at 60 Hz (and harmonics) was found to be present in the data, and is attributed to AC line noise, which could be reduced with refinements of the setup.

The first noticeable characteristic of the data for one embodiment of this disclosure in FIG. 2(a) is the increased granularity of the HEK cell measurements as compared to the relatively smooth curve that is produced without cells. In addition, the slopes appear different as highlighted by the fact that both curves start out relatively similar to each other at around 10 Hz but diverge significantly at higher frequencies, particular above 10 kHz. The unique morphology of the HEK cell curve might be indicative of cell motility. The cells were not fixed to the surface, and were free to move around. We used this property to avoid using a micromanipulator to position the cells. As such, during each measurement the cells can move slightly and even vibrate. The velocities of the cells were measured by analyzing the distance they moved per measurement. Cells on the devices moved slower than those away from the devices. On the device, cells moved on average about 0.6 microns per minute. The cells away from the device ranged from about 0.6 to about 12 microns per minute. Those that moved quickly are believed to be above the surface. Based on the focal plane, the slower cells, including those on the devices, are believed to be in contact with the surface which retards their motion. Other cell characteristics, such as ion channel kinetics or membrane reactions to the nanotubes might also be related to granularity of the curve. The sharp differences in impedance with and without cells suggest that an impedance measurement between closely spaced nanoprobes is capable of detecting the presence of the HEK cells in said embodiment of this disclosure.

To demonstrate the versatility of certain embodiments of this disclosure, different types of cells were tested. In addition to the HEK cells, neuron cells from mice and yeast cells were studied. High-resolution images of the three types of cells are shown in FIGS. 3(a)-3(c). A big difference between the cells is their size and shape. The HEK cells are round and average in size between about 16 to about 30 microns, while the yeast cells range from about 6 to about 10 microns. In contrast, neurons have a more amorphous shape and range in size from about 18 to about 28 microns. Both the HEK and neuron cells are larger than the probe spacing [about 6 microns], while the yeast cells are similar or larger.

The difference between cell size and probe spacing in certain embodiments of this disclosure allows for a single cell measurement with a small degree of sub cellular resolution for the three cell types. The resulting impedance spectra of the cells were normalized by dividing out their case without cells on the electrodes. The normalized impedance spectra are shown in FIGS. 3(d)-3(f). A value of 1 is an indication that the measurements with and without cells are similar and can be thought of as a baseline. The dotted line represents this base line. The data without cells, which makes up the baseline, did not appear to be significantly affected by measurements with cells.

The different cell types appear to have distinct properties in their impedance spectra. The HEK spectrum starts out at around 10 Hz but then increases to around 25 at high frequencies. This is in stark contrast to both the yeast cells and the neuron cells, which tend to trend less than one. For the yeast cells the affect is less pronounced and only at low frequencies. Neuron cells overall experience a drop in impedance when a cell is over the electrodes. This seems unexpected since adding a dielectric material in between the electrodes should raise the impedance. The drop could be attributed to the neurons themselves. It could be possible that the neuron cells were interacting with the carbon nanotubes. Neuron cells have been known to respond to electrical stimuli from electrodes including nanotubes. If the nanotube electrodes could stimulate the neuron cells, they could respond by releasing a range of ions which change the conductivity of the media around the cells and thus between the nanoprobes.

Both the yeast and the neuron cells impedance traces have structure to their curves. Interestingly though, the granularity of the curves appears to be more than that of the HEK cells. This could be attributed to the fact that the HEK cells are model cells, designed to study ion channels. As such, the ions around the HEK cells are limited to potassium and sodium ions which are used to maintain osmotic pressure across the membrane and to maintain a membrane potential, thus creating less variation in the extracellular material surrounding the cells as compared to the yeast and neuron cells. The extra types of ions surrounding the yeast cells include organic acid from metabolizing sugar and oxygen, while the neuron cell contain additional ions such as $Ca^{+2}$ and amino acids used by the cells for communications. The three different extracellular environments could create unique structures in the impedance spectra for the three types of cells.

Another possible explanation of the difference in the spectra for each type of cell is cell motility. The neuron cell's velocities ranged from about 0.9 to about 16 micron per minute, where the higher velocity cells were above the surface. This is similar to the HEK cells which ranged from about 0.6 to about 12 microns per minute. The yeast cell's velocity could not be measured due to the complete cell coverage of the field of view, which prevented identification of any one cell for tracking. While the cell motility could play a role in the impedance spectra, the data does not seem to support it. The neuron cells are the largest and the yeast cells are the smallest, while the HEK cells are in the middle in terms of size. It is reasonable to consider the cell motility to be dominated by Brownian motion, which is dependent on size. This effect does correlate with the neuron cell's velocity being slightly larger than the HEK cells. If the variation in the impedance spectra were dependent on motility than the measured impedance spectras would deviate from their respective baseline, either as increasing or decreasing impedance, with the amount of deviation being related to the size of the cell. However, this does not seem to be the case. Instead the largest (neuron cells) and the smallest (yeast cells) both experience a drop in impedance while the middle sized cells (HEK cell) experience a rise in impedance. While it is conceivable that cell motility can play a role in the impedance spectra, its influence could be a secondary effect and not a primary one.

In order to better understand the roles the nanotubes play, impedance measurements were repeated using embodiments of this disclosure where nanotube were not deposited. FIG. 4(a) shows an SEM image of the devices, which is made up of a pair of about 1 micron wide electrodes with about 44 nm apertures 106 in the silicon nitride layer, leading down to the metal. During nanotube deposition, the nanotubes would deposit within these apertures 106. Without the nanotubes, the metal at the base of the nano-sized apertures 106 generates the electric field used in the impedance measurements as opposed to the sharp tip of the nanotube.

The resulting impedance spectra for HEK cells, neuron cells, and yeast cells are shown in FIGS. 4(b)-4(d) respectively. The most striking feature is the lack of shift on average between measurements taken with and without cells. This is in stark contrast to those taken with nanotubes. With nanotubes as probes, there was significant increase in impedance with HEK cells and a significant drop with neuron and yeast cells. The nanotubes of these embodiments obviously play an important role in the impedance measurements of the various cell types, and may even be interacting with the cells. Three other possibilities could be occurring as well. The first is that without the nanotubes, the approximately 75 nm deep holes (aspect ratio of about 2:1 [depth: diameter]) could be deep enough to reduce the sensitivity of the devices as compared to the nanotube devices. Planar geometry microscale probes can detect single cells using impedance spectroscopy when the cells are in close proximity (e.g., in direct contact).

In this case the aperture geometry is needed to control the deposition of the SWNTs 110, which precludes direct contact with the cells to our probes unless there are SWNTs 110. The geometry of the SWNTs 110 may also increase the sensitivity of the impedance measurement. The relative sharp tips of the nanotubes (about 1 nm) are known to have electric field enhancements. This focuses and increases the field strength at the nanotubes tips, thus allowing the measurement to be more sensitive than the about 44 nm planar electrodes.

Another potential reason for increased sensitivity is in the difference in materials. Without nanotubes, Cr (used as the metal at the bottom of the apertures 106) is the electrode surface. Metals such as Cr may not be as good as carbon (which is relatively inert and biocompatible) for electrodes used in bio experiments, potentially due to oxidation and other possible electrochemical effects.

The field enhancement from the nanotubes will concentrate the field lines closer together, thus increasing its strength as compared to the relatively flat electrode surface at the bottom of the about 44 nm aperture. This effect is similar to the tip enhancements in atomic force microscopy surface-enhanced Raman spectroscopy (AFM-SERS) of particles, where the sharp tips enhance and focus the electric fields to a small part of the particle. This gives a strong interaction with the mobile charges in and around the cell creating relatively large polarization effects that may be responsible for the changes in impedance. It must be pointed out that the interface between the CNTs and the metal interconnects has not been characterized for this deposition method. Even though CNTs can form low resistance contacts with metals such as Cr, Ti, and Fe, it does not necessarily follow that after electrophoresis deposition the contacts are ohmic. However, embodiments of the device having a structure as disclosed herein does enable one to detect and distinguish between the cell types that were measured. Keeping these factors in mind, it is conceivable that the measurement from the nanotubes is occurring on the two parts of the cell membrane which are closest to the two nanotube probes, as opposed to a whole cell measurement.

Embodiments of this disclosure allow for demonstration of a sub-10 nm probe using the current generation of CMOS process technology (including lithography). The method uses electrophoresis in conjunction with nanoscopic lenses to deposit the SWNTs 110 in a controlled fashion. Since the deposition is done at room temperature, it does not suffer the deleterious effects normally imposed by growing SWNTs 110 using chemical vapor deposition (CVD) at relatively high temperatures (e.g., above 300 C) or the need to control the diameter of the SWNT using lithography that cannot be used in the current generation of manufacturing technology.

Figure 5:
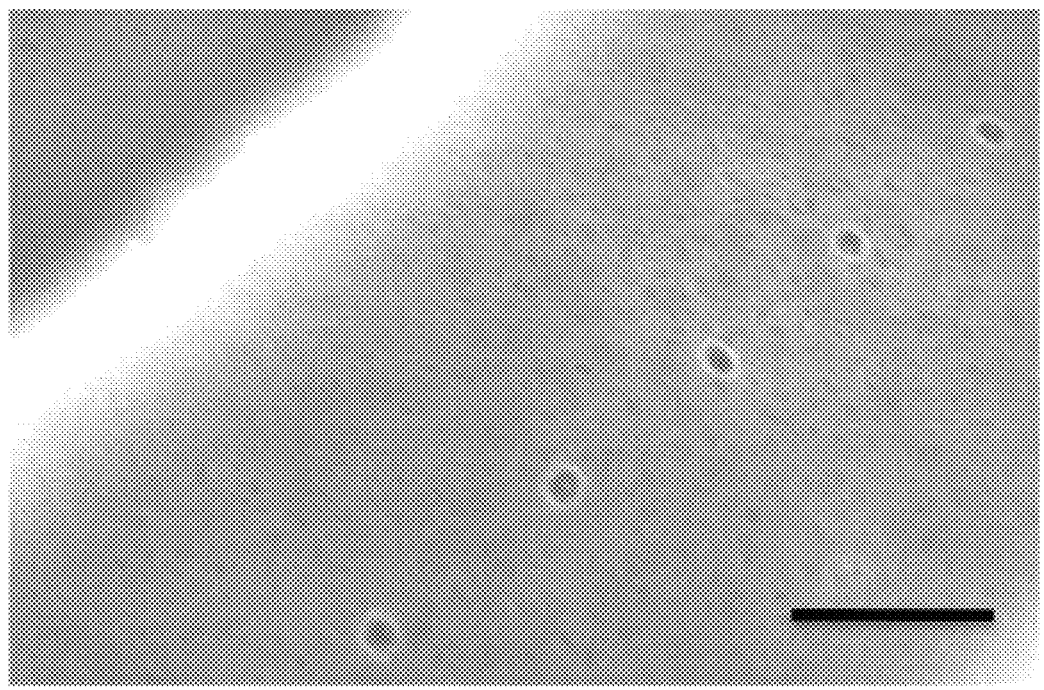
FIG. 5 is an SEM image of SWNTs 110 deposited using electrophoresis on Ti at the base of approximately 30 to approximately 40 nm apertures (approximately 75 nm deep) spaced approximately 200 nm apart, wherein the scale bar is approximately 200 nm.

The limit to the spacing between SWNTs 110 is set by current CMOS process technology, which is established by the International Technology Roadmap for Semiconductors (ITRS). Apertures 106 in thin dielectrics that are about 30 to about 40 nm in diameter are readily available in the current generation for DRAM contact apertures 106. When the limits to level-to-level overlay are taken into account, the practical limitation using current CMOS process technology is about 50 nm wide interconnect lines with about 50 nm spacing, which leads to center-to-center aperture spacing of about 100 nm. The current generation of aperture sizes does not appear to limit the electrophoresis deposition of certain embodiments of this disclosure as indicated in FIG. 5. In this case SWNTs 110 that were presorted to be less than about 180 nm long were deposited on Ti metal at the base of about 30 to about 40 nm apertures 106 (about 75 nm deep) spaced about 200 nm apart.

Embodiments of this disclosure show a successful fabricated device for detecting cells using vertically deposited carbon nanotubes. Said embodiments are planar and have small enough inter-nanotube spacing to allow for single cell measurements using pairs of probes. Certain embodiments also utilize standard CMOS technologies and self-alignment allows for scaling of future devices down to the nanometer scale. The method of embodiments of this disclosure can reduce complexity and cost compared to other technologies. In addition, in certain embodiments multiple devices of the same kind could be arranged in a high-density array, allowing for simultaneous measurements across a single cell or a group of cells.

As disclosed above, in a tested embodiment of this disclosure, the device successfully performed impedance measurements on HEK cells. Neurons from mice and yeast cells, which exhibited different spectra from those of HEK cells, were also tested using one or more embodiments of this disclosure. Measurements with and without cells showed a significant difference, indicating that cells can be detected with embodiments of this disclosure. Also, the difference in the spectrum between different cell types indicates that the devices could distinguish between different cell characteristics. In addition, since the test cells were not actively positioned or impaled, measurements were made without significantly disturbing the cells. As presented above, the results were tested against embodiments without nanotubes which proved that the nanotubes affected the sensitivity.

In addition to testing the existence of cells, embodiments of this disclosure can be used to probe only small sections of the cell membrane for any suitable purpose. The unique spectrums of impedance as a function of frequency for the three different cell types tested shows that the devices disclosed herein are effective in studying electrostatics and dynamics of various cells. Such a device can be used for any suitable purpose, such as, to look at action potentials, study ion channels, membrane potentials, and sub cellular processes with a high degree of spatial resolution (nanometer range) without disturbing the cells or requiring the cells to be immobilized.

Further disclosed herein is a method to detect a single cell and/or a plurality of single cells. The method includes sensing the change in impedance between two carbon nanotubes (e.g., SWNTs 110 as disclosed herein) that are spaced at a distance that is less than the size of the cell to be detected. Using such a method, single cells can be detected label free and the spatial resolution (because of the size of the probe) allows for detection of single cells that are too small to perform traditional electrophysiology.

Also disclosed herein is a method to detect that a carbon nanotube was successfully deposited in the apertures 106 and functioning. The method to determine the presence of single wall carbon nanotubes (SWNTs 110) deposited by electrophoresis on metal at the base of an about 30 nm to about 60 nm aperture in an insulating film is described below. The method allows for rapid diagnostics of invidious devices regardless of their numbers, which can be important when the number of devices is high, for example, over one million. The method is also scalable to wafer level, as may be useful for mass production for commercialization. The diagnostics are performed by performing current vs. voltage (IV) measurements against a single device (which would contain a SWNT in an about 30 nm to about 60 nm aperture) against an external platinum electrode and/or between individual devices. Both the devices and the platinum electrode are immersed in a conductive liquid, such as phosphate buffer. The resulting current would be an indication of the presence of the SWNT. It is also possible that the IV curves could represent the quality of contact between the SWNT and the electrode that it is deposited on, based on the shape of the curves.

Figure 6A:
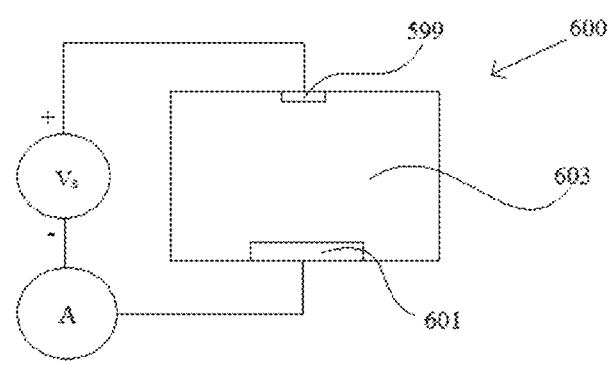
FIG. 6(a) shows a schematic of an experimental setup for testing devices to a Pt reference electrode.
Figure 6B:
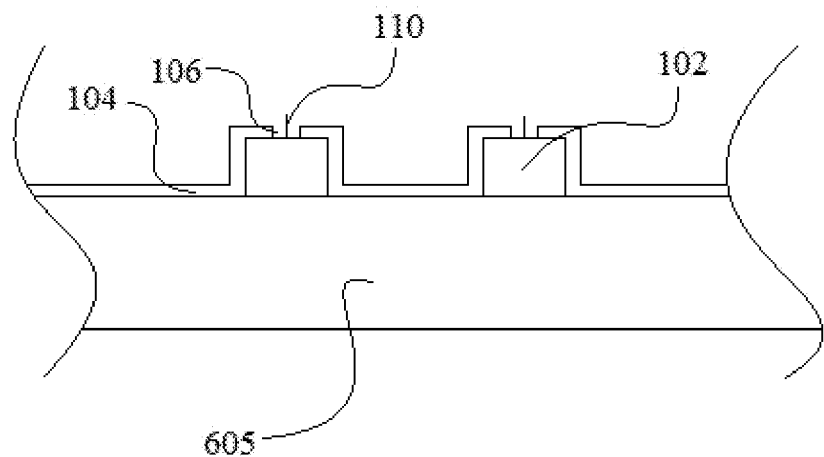
FIG. 6(b) shows a schematic of an experimental setup for device to device with nanotubes.
Figure 6C:
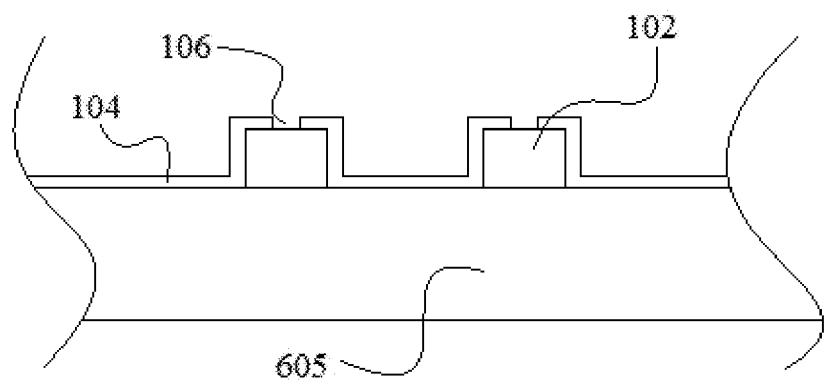
FIG. 6(c) shows schematics of the experimental setup for device to device without nanotubes.

To demonstrate this, IV measurements were performed on chips 599 with SWNTs 110 deposited and without SWNTs 110. The experimental setup 600 is shown in FIGS. 6(a)-6(c). The devices 100 on the chip 599 comprise an electrode 102 (e.g., a titanium electrode) with about 75 nm of an insulating layer 104 (e.g., a low stress silicon nitride (SiNx)) deposited on top with about 30 nm to about 60 nm diameter apertures 106. The assembly can be disposed on a substrate 605. SWNTs 110 were deposited in some of the apertures 106 using electrophoresis. A HP4140B pico-ammeter was used to apply the external voltage (Vs) and measures the resulting current (A). The chip 599 and a reference electrode 601 (e.g., a platinum electrode) were separated by about 1 cm and immersed in a buffer solution 603 (e.g., a phosphate buffer solution). The chip 100 was connected to the positive terminal and the platinum electrode 601 to the negative terminal.

FIG. 7(a) shows IV curves of devices recorded using phosphate buffer solution as the conducting medium to a platinum electrode. The plots are of devices with SWNTs 110 (Red Circles) and without SWNTs 110 (Black Squares) against a platinum electrode. The curve for devices without SWNTs 110 is plotted separately in the insert. The curves are averaged over 12-14 devices. There is a stark contrast in the range of current shown. Devices without SWNTs 110 have a current range in the hundreds of pico-amps while devices with SWNTs 110 show a current range in the tens of nano-amps. The two orders of magnitude difference can be attributed to presence of SWNTs 110. Another difference in the IV curves are in the shape. Devices without SWNTs 110 exhibited a symmetrical curve but offset such that zero current occurs in the range of about −0.2V to about −0.47V. The range is from the hysteresis, which is typical in electrochemical systems. Devices with SWNTs 110 also show an offset from about −0.2V to about −0.32V. In addition the shape of the curve is asymmetrical, with larger currents occurring in the negative voltage region.

FIG. 7(b) shows IV curves for the case where device electrode 102 to device electrode 102 measurements were made as opposed to a reference electrode 601. The plots are of devices with SWNTs 110 (Red Circles) and without SWNTs 110 (Black Squares) against another device. The curve for devices without SWNTs 110 is plotted separately in the insert. As is the case with the device to Pt electrodes, the devices with nanotubes produces orders of magnitude higher current and a significantly different shaped IV curves compared to devices without nanotubes. The differences could be attributed to two factors. One is that without the nanotube, the phosphate buffer has to enter the about 30 nm to about 60 nm aperture in SiNx to reach the Ti metal. The SiNx layer is hydrophobic making it very difficult for the ions in the solution to react with the Ti metal at the bottom of the apertures 106. This could cause the reduction in current observed without SWNTs 110. When SWNTs 110 are present, they can extend beyond the SiNx layer allowing direct access to the phosphate buffer, making the reaction with ions in the solutions significantly easier and allowing higher currents than without SWNTs 110. The asymmetrical structures of the IV curve with SWNTs 110 can be attributed to one or more of the electrochemical reactions and the contact interface of the nanotube to the Ti metal and will be described in detail.

Also disclosed herein is a method to get detailed information about the functioning of the cell, which can be derived from the impedance measurement. Biological cells have proteins that can pass ionic charge through the cell membrane when activated by an electric field (voltage). They are referred to as voltage gated channels. The activity of these ion channels are traditionally monitored using the patch-clamp technique which involves puncturing the membrane to make an electrical connection with the fluid inside the cell. Fluctuations in the current or voltage of the cell relative to an electrode placed in the cell media outside of the cell are a direct measure of the activity of the ions passing through the protein channels and therefore the functioning of those channels. The activity of the channel (passing ions through the cell membrane) is a direct indication of the cell health. In some cases ion channels also while functioning normally open at a specific rate, which can be characteristic for that ion channel. The technique that is described herein includes a way to excite the ion channel to open with an oscillating electric field (AC voltage) and measure the frequency or the natural rate for that ion channel. The signal from the cell opening can be detected as a local change in conductance in the fluid around the cell, which will be evident as a fluctuation of the impedance between two carbon nanotube bioprobes that are in close proximity to the cell.

Figure 9:
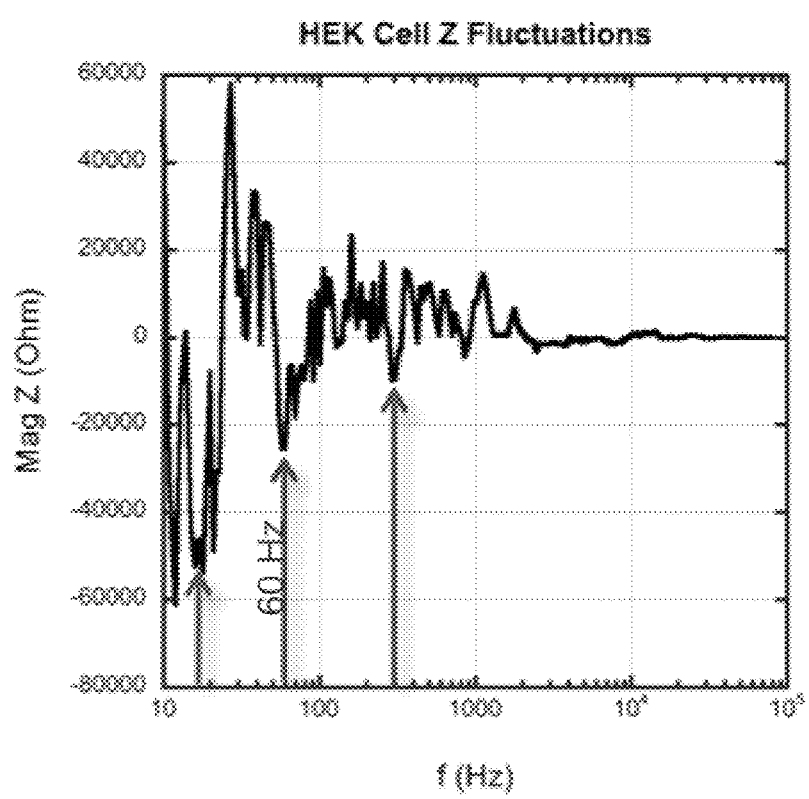
FIG. 9 shows a plot of experimental data created as a function of the data of FIG. 8 as described herein.

The method to derive the activity of the ion channels is shown by example of an additional analysis of the plot in FIG. 2(a). There are two components to the change in impedance relative to the data taken when no cells were present. The first contribution comes from the dielectric properties of the cell including the insulating membrane. In the case in FIG. 2(a) the average affect is to increase the impedance. Further inspection of the same curve shows that there are significant fluctuations in the impedance as a function of frequency. The assumption is that the amplitude of the AC voltage creates an electric field large enough to trigger the ion channels in close proximity of the bioprobes to open. The method is to fit the average magnitude of the impedance as a function of frequency to a mathematical function and then subtract the best fit to that function from the impedance data. The remainder contains the fluctuations relative to the average behavior. An example of the procedure is shown in FIGS. 8 and 9.

In this example the average impedance behavior was fit to the function:

$$Z_P(\omega)=K^{-1}(i\omega)^{-\alpha},$$

which is a straight line when displayed on a log-log plot as shown in FIG. 8, where the straight line is the fit to the data.

The fit is subtracted from the data in FIG. 8 and plotted in FIG. 9 using a log-linear plot to highlight the low frequency region in the data where the fluctuations have the highest amplitude. These peaks and troughs in the fluctuations can then be compared to characteristic rates of ion channels known or suspected of being present in the cell. This could be used to check the health of a known cell or as a further screening of cells to determine differences between cells including cell health and/or cell type.

Any of the herein disclosed methods and/or portions thereof can be implemented with any suitable circuitry, computer, software, hardware, and/or any other suitable automation.

While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A method, comprising:
   providing a device operable to determine the presence of a single biological cell and/or a state of a single biological cell in a fluid medium, wherein the device comprises a first nanotube disposed on a first electrode and a second nanotube disposed on a second electrode, wherein the first and second nanotubes are spaced apart at a distance that is equal to or smaller than the single biological cell,
   positioning the first nanotube and the second nanotube in contact with the fluid medium, and
   testing a conductance and/or an impedance of the device between the first and second nanotubes such that when one of the nanotubes is in a position proximate to but not penetrating the single biological cell, the presence of the single biological cell and/or a state of the single biological cell is detected.

2. The method of claim 1, wherein device is positioned within an electrolytic fluid.

3. The method of claim 1, wherein the testing of conductance and/or impedance is done between the first nanotube and the second nanotube, the method further comprising determining a state or type of a biological cell based on the conductance and/or impedance.

4. The method of claim 3, further including exciting an ion channel of a biological cell with an oscillating electric field, measuring a natural rate of opening for the ion channel, and detecting a local change in conductance in the fluid around the cell, wherein the conductance is evident as a fluctuation of impedance between the first nanotube and the second nanotube.

5. The method of claim 4, further comprising obtaining plural measurements of impedance, determining an average magnitude of the impedance as a function of frequency of the oscillating electric field, fitting an average magnitude of the impedance as a function of such frequency to a mathematical function and subtracting the best fit to that function from the impedance to determine fluctuations relative to the natural rate of opening.

6. The method of claim 5, further comprising comparing peaks and troughs of fluctuations of impedance to the natural rate of opening of the ion channel known or suspected to be present.

7. The method of claim 6, wherein the determined state includes a cell health or a cell type.

* * * * *